(12) United States Patent
Lombardo et al.

(10) Patent No.: US 10,588,616 B2
(45) Date of Patent: Mar. 17, 2020

(54) THREADED KNOTLESS ANCHOR

(71) Applicant: Linvatec Corporation, Largo, FL (US)

(72) Inventors: Giuseppe Lombardo, Trinity, FL (US); Steven E. Fitts, New Port Richey, FL (US); Peter C. Miller, Largo, FL (US)

(73) Assignee: LINVATEC CORPORATION, Largo, FL (US)

( * ) Notice: Subject to any disclaimer, the term of this patent is extended or adjusted under 35 U.S.C. 154(b) by 198 days.

(21) Appl. No.: 15/902,026

(22) Filed: Feb. 22, 2018

(65) Prior Publication Data

US 2018/0177500 A1    Jun. 28, 2018

Related U.S. Application Data

(60) Continuation of application No. 15/333,318, filed on Oct. 25, 2016, now Pat. No. 9,924,936, which is a division of application No. 14/540,634, filed on Nov. 13, 2014, now Pat. No. 9,526,492.

(51) Int. Cl.
*A61B 17/04* (2006.01)
*A61B 90/00* (2016.01)

(52) U.S. Cl.
CPC ...... *A61B 17/0401* (2013.01); *A61B 17/0469* (2013.01); *A61B 2017/044* (2013.01); *A61B 2017/0409* (2013.01); *A61B 2017/0445* (2013.01); *A61B 2017/0451* (2013.01); *A61B 2090/0811* (2016.02)

(58) Field of Classification Search
CPC . A61B 17/04; A61B 17/0467; A61B 17/0401; A61B 17/0469; A61B 2017/0409
See application file for complete search history.

(56) References Cited

U.S. PATENT DOCUMENTS

| 5,102,421 A * | 4/1992 | Anspach, Jr. ...... | A61B 17/0401 606/232 |
| 5,643,320 A * | 7/1997 | Lower ................ | A61B 17/0401 606/104 |
| 2006/0116719 A1 * | 6/2006 | Martinek ........... | A61B 17/0401 606/232 |

* cited by examiner

*Primary Examiner* — Vi X Nguyen
(74) *Attorney, Agent, or Firm* — Frederick J M Price; Bond, Schoeneck & King, PLLC

(57) ABSTRACT

A knotless suture anchor assembly for engaging a bone tunnel and holding suture therein to knotlessly secure said suture to soft tissue including an elongated generally cylindrical hollow outer member having an axial lumen, an outer surface with projections for engaging the wall of the bone tunnel, a distal end and a proximal end; and an elongated, generally cylindrical inner member having an axis, a proximal end and a distal end, the distal end having a transverse passage for receiving suture therethrough, the transverse passage having a proximal and distal end and adapted to receive a plurality of sutures in said eyelet, the inner member adapted to move coaxially relative to the outer member between a distal, suture-unlocked position and a proximal, suture-locked position.

2 Claims, 19 Drawing Sheets

US 10,588,616 B2

THREADED KNOTLESS ANCHOR

CROSS REFERENCE TO RELATED APPLICATIONS

This application is a continuation of U.S. patent application Ser. No. 15/333,318, filed on Oct. 25, 2016, which is a divisional of U.S. patent application Ser. No. 14/540,634, filed on Nov. 13, 2014, the contents of each is relied upon and incorporated herein by reference in its entirety, and the benefit of priority under 35 U.S.C. § 120 is hereby claimed.

FIELD OF THE INVENTION

The invention relates to suture anchors for securing sutures and other filamentary material to soft tissue. More particularly, the invention relates to suture anchors for securing sutures and similar filamentary material to soft tissue to reattach the soft tissue to bone. Still more particularly, the invention relates to suture anchors for knotlessly securing suture and filamentary material at a surgical site.

DESCRIPTION OF THE RELATED ART

In situations where ligaments or other soft tissue are being secured to bone, a suture anchor is commonly employed. The anchor is inserted into a generally preformed hole in the bone and a suture or similar filamentary material extends from the anchor and is attached to the soft tissue to be secured to the bone. As used herein, the term "bone hole" is used interchangeably with "bone tunnel" and the term "suture" includes monofilament or multi-filament suture as well as any other metallic or non-metallic filamentary or wire-like material suitable for performing the function of a suture including both absorbable and non-absorbable materials.

Whether such surgical procedures are done open or closed, in most instances, the suture must be tied to the soft tissue so that a knot must be formed. When such procedures are done arthroscopically or endoscopically (i.e., closed), creation of a knot is somewhat difficult. As a result, knotless suture anchors have been recently developed to avoid the knot tying step.

One example of a knotless suture anchor is shown in U.S. Pat. No. 6,692,516 (West Jr. et al.), assigned to the assignee hereof and incorporated by reference herein. This patent discloses an expandable metallic knotless suture anchor, the design of which is difficult to implement with the use of non-metallic material. As used herein, the term "expandable" means the diameter of the device increases when it is deployed/anchored in the bone.

U.S. Published patent application 2005/0055052 (Lombardo et al.) discloses a knotless suture anchor which may be made of bioabsorbable material. This application is assigned to the assignee hereof and incorporated by reference herein. While the design disclosed in this reference is compatible with bioabsorbable material, the design is a press-fit design and is limited in the types of surgical procedures for which it is suitable. As used herein the term "press-fit" means the anchor is not turned into a bone tunnel and the diameter of the device is substantially the same before and after deployment/anchoring in the bone.

Some knotless suture anchors have been developed and one such example is disclosed in U.S. Pat. No. 8,663,279 (Burkhart et al.). This device consists of a two part anchor in the form of an inner implant, which receives suture attached to soft tissue to be repaired, and an outer, cannulated and threaded fixation device designed to be rotated relative to the inner implant whereby the outer device progressively advances toward the inner implant and frictionally engages the suture against the wall of the bone tunnel without the need to tie a knot. One difficulty with this type of system is the primary reliance on the quality of bone in the bone tunnel and the difficulty of gauging the relative positions of the inner and outer components when the components are engaged, thereby making it difficult to optimize the friction fit.

Therefore, the need exists for a simple to use suture anchor which secures suture without needing to tie a knot and which removes the primary dependency of suture security from bone quality.

It is an object of this invention to produce a non-metallic suture anchor suitable for knotlessly securing suture to attach a first body tissue to a second body tissue.

It is another object of this invention to produce a knotless suture anchor suitable for repairing a soft tissue tear, for example, a torn rotator cuff, and re-attaching it to bone, for example, the humeral head.

It is still another object of this invention to provide a method of determining the relative positions of the components of a knotless suture anchor in order to optimize the force with which the suture is held by the anchor. It is a further object of this invention to provide an apparatus for performing this method.

It is also an object of this invention to provide a method and apparatus for knotlessly securing a suture to a suture anchor where the quality of the fixation of the suture is independent of the quality of the bone into which the suture anchor is placed.

SUMMARY OF INVENTION

These and other objects of this invention are achieved by the preferred embodiment disclosed herein. This invention is a knotless suture anchor assembly for engaging a bone tunnel and holding suture therein to knotlessly secure the suture to soft tissue. The assembly comprises an elongated generally cylindrical hollow outer member having an axial lumen, an outer surface with projections for engaging the wall of the bone tunnel, a distal end and a proximal end and an elongated, generally cylindrical inner member having an axis, a proximal end and a distal end, the distal end having a transverse passage for receiving suture there through. The transverse passage has a proximal and a distal end and is adapted to receive a plurality of sutures in the eyelet. The inner member is adapted to move coaxially relative to the outer member between a distal, suture-unlocked position and a proximal, suture-locked position. A suture joins the soft tissue to the anchor and is directed along a tortuous path from the soft tissue to the bone tunnel, distally between the outer member and the wall of the bone tunnel, through the transverse passage, and proximally between the outer member and the wall of the bone tunnel. A locking means is interposed between the inner and outer members and is coaxially movable between a suture-unlocked configuration, in which the inner member is moveable relative to the outer member so the suture is slidable along the path, and a suture-locked configuration in which movement of the inner member relative to the outer member is prevented and the suture is crimped between the proximally facing, distal end of the eyelet and the distal end of the outer member. The invention further includes means for moving the inner member proximally (relative to the outer member) from the suture-unlocked position toward the suture-locked position wherein the suture is crimped between the inner and outer members, means for moving the outer member distally from the suture-unlocked position toward the suture-locked position and means for locking the inner member to the outer member to maintain the inner and outer members in the suture-locked position.

Another aspect of the invention is a method of knotlessly securing soft tissue to suture in a bone tunnel and to a suture anchor comprising the steps of providing a knotless suture anchor as described above, providing an indicator which is viewable from outside the bone tunnel and which indicates the position of selected components of the suture anchor relative to other selected components of the suture anchor at predetermined points in the process of securing the suture, and locking the components of the suture anchor together.

DESCRIPTION OF THE PREFERRED EMBODIMENTS

Figure 1:
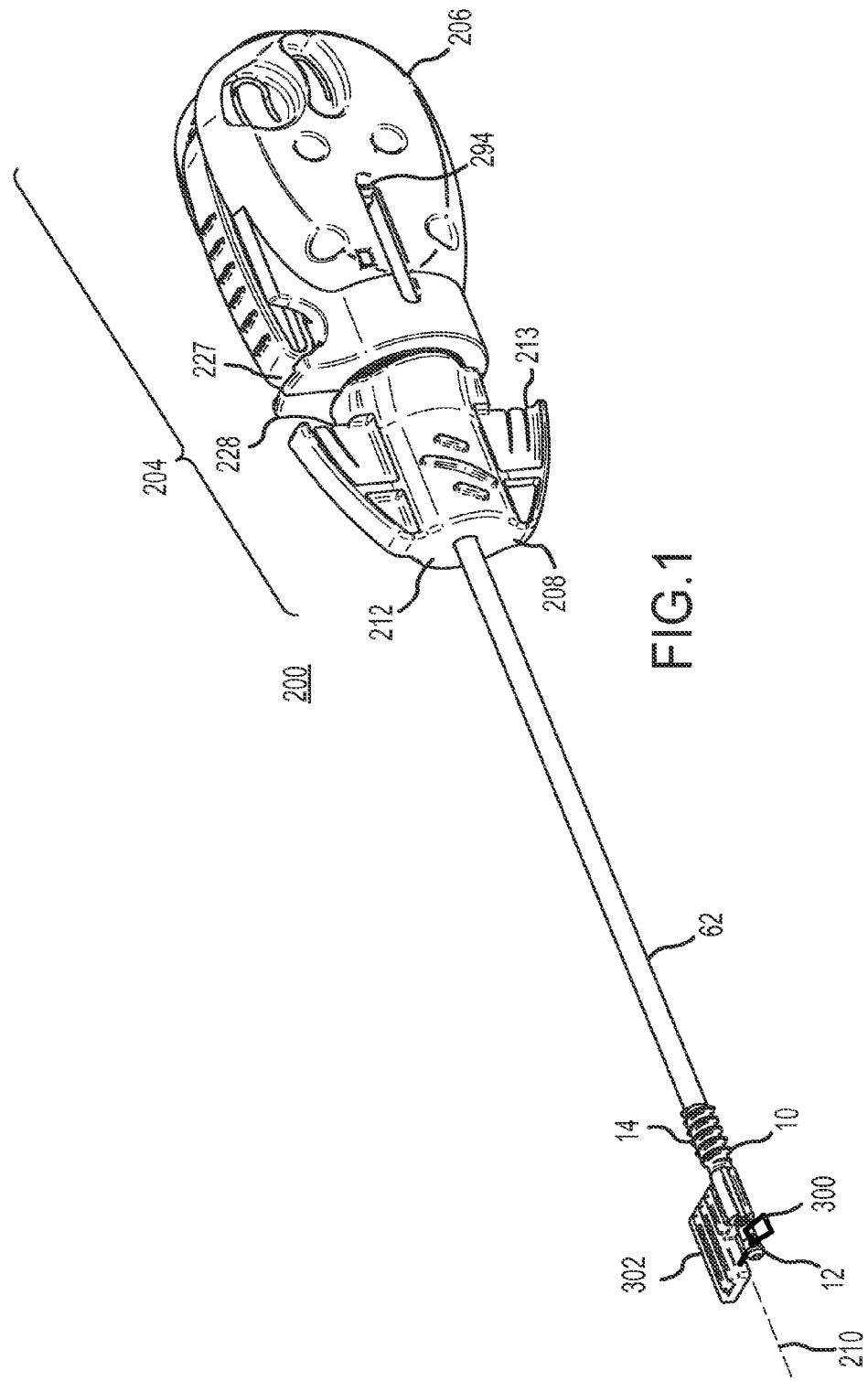
FIG. 1 is a perspective view of the preferred embodiment of the driver and anchor assembly showing the driver handle with the trigger lever in the first position.
Figure 2:
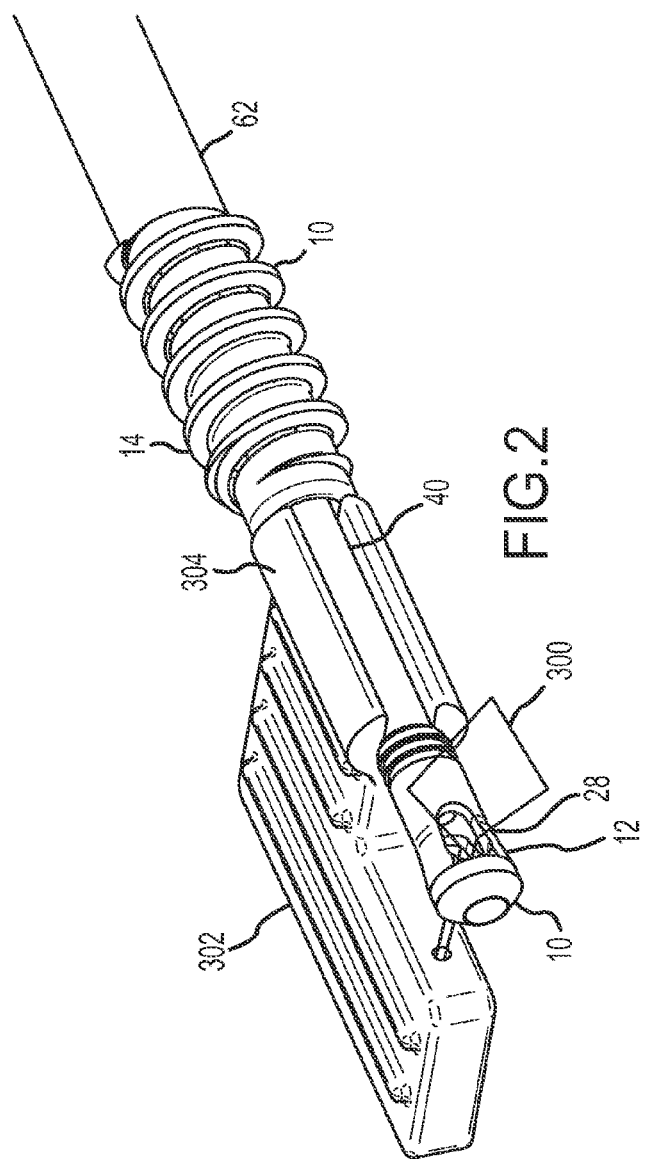
FIG. 2 is an enlarged view of the distal end of FIG. 1.
Figure 3:
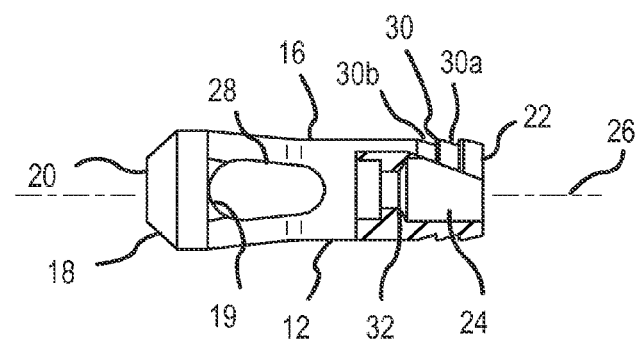
FIG. 3 is a side view of the inner anchor member with a partial cross-section through the proximal end.
Figure 10:
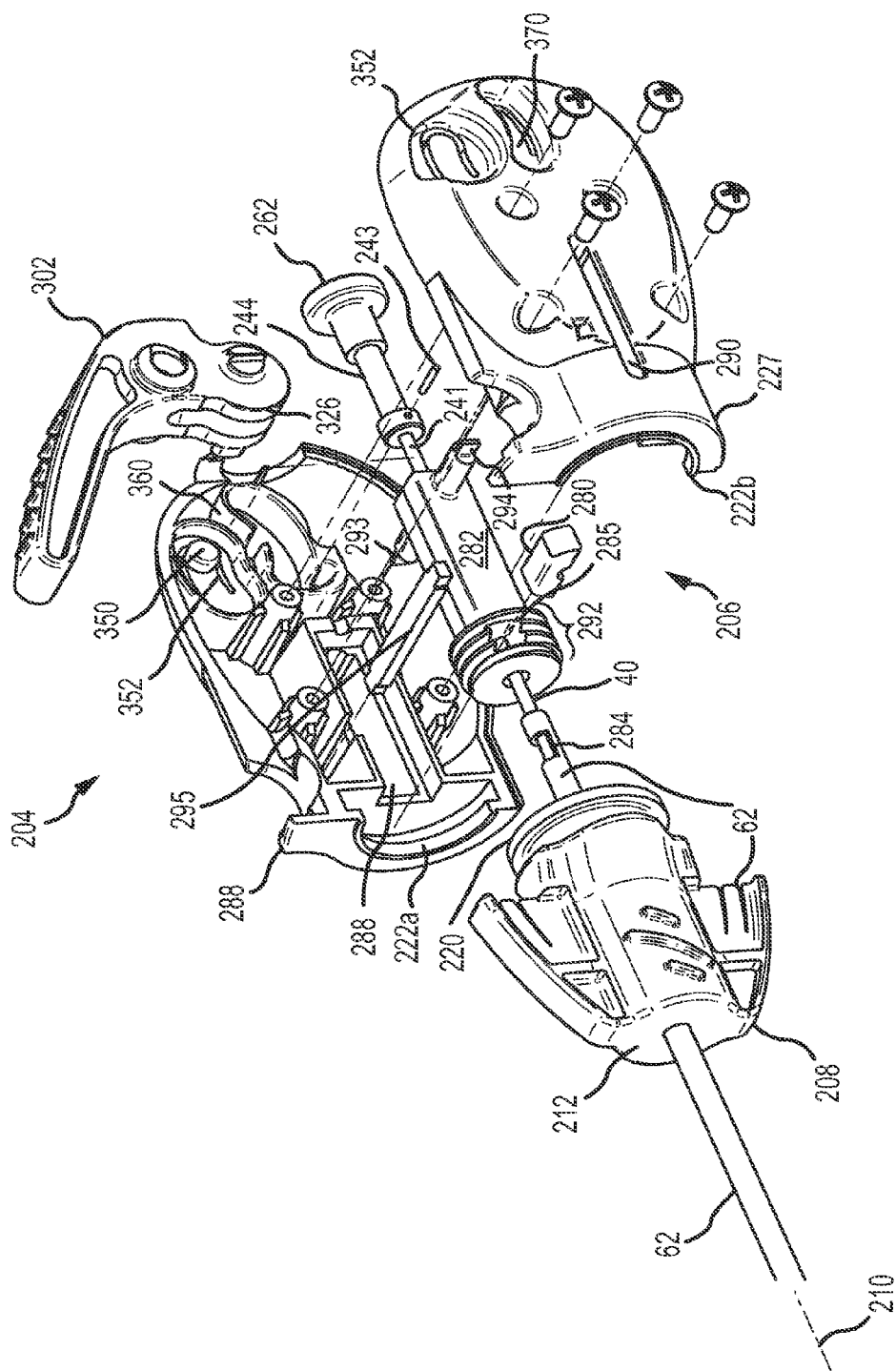
FIG. 10 is an exploded perspective view of the handle of the driver.
Figure 14:
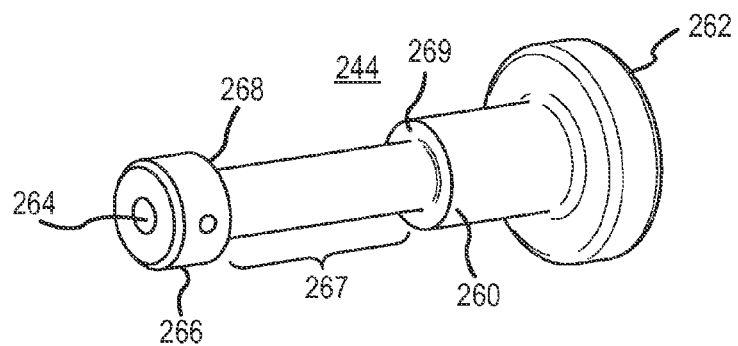
FIG. 14 is a perspective view of the actuator coupler.

Referring to FIGS. 1 and 2, knotless suture anchor 10, constructed in accordance with the principles of this invention, comprises an inner anchor member 12 and an outer anchor member 14. As will be understood below, anchor members 12 and 14 are components of anchor 10 which are initially axially spaced from each other at the distal end of driver 200 and are joined to the proximal end of driver 200 by respective connecting shafts. The anchor members are designed to become joined in order to anchor a suture at the surgical work site between components of anchor 10 as well as between the wall of a preformed bone tunnel and the facing surfaces of anchor 10. Referring now to FIG. 3, inner anchor member 12 comprises a generally cylindrical elongated body 16 having a distal end 18, a distal tip 20, a proximal end 22 and an axial lumen 24 aligned with axis 26. Member 12 further comprises a transverse eyelet 28 adjacent its distal end 18. The distal-most end of eyelet 28 is adjacent a transverse compression surface 19 which, as will be understood, ultimately compresses any suture in eyelet 28 against the distal end of outer anchor member 14. One or more annular locking grooves 30 are provided at the proximal end 22 of inner member 12. Member 12 has an axially aligned actuator engaging shoulder 32 which enables member 12 to be frangibly attached to a narrowed section 34 at the distal end 36 of actuator shaft 40 (best seen in FIG. 5). Actuator shaft 40 joins inner anchor member 12 to actuator coupler 244 situated at the proximal end of driver handle 204 as best seen in FIGS. 10 and 14.

Figure 4:
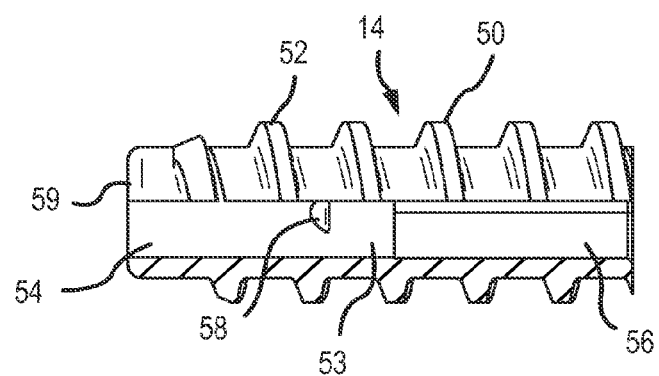
FIG. 4 is a side view of the outer anchor member with a partial cross-section.
Figure 7:
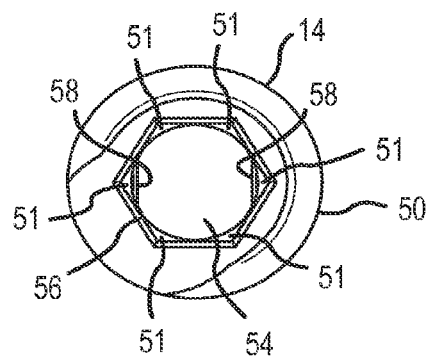
FIG. 7 is a right end view of FIG. 4 without suction.

Referring now to FIGS. 4 and 7, outer anchor member 14 comprises a cannulated sleeve 50 with projections which, in the preferred embodiment, comprise a threaded exterior surface 52. Sleeve 50 has an axially aligned lumen 53 with a distal portion 54 having a cylindrical cross-section, a proximal portion 56 having a non-circular (e.g., hexagonal) cross-section and a pair of diametrically opposed projections 58 on its interior surface (only one of which is seen in FIG. 4). As seen in FIG. 7, a shoulder 51 is produced at the junction between lumen portions 54 and 56. Projections 58 are adapted to engage one of the grooves 30. When the projections are engaged with a groove, inner member 12 is prevented from moving distally, thereby effectively locking the inner and outer members 12 and 14 together as will be understood below. In the preferred embodiment a plurality of grooves 30 is provided so that the two components 12 and 14 can be locked at a selected position relative to each other depending on the number and size of sutures used. Eyelet 28 is created to be large enough to accept a predetermined number of sutures. In the preferred embodiment, eyelet 28 can receive one to three strands of (preferably) braided suture which has a diameter of approximately 0.63 mm. Use of sutures of this size allows the proximal end of eyelet 28 to accommodate a selected number of sutures while also enabling an acceptable degree of compression of the sutures in the eyelet when anchor 10 is deployed (i.e., when the inner and outer anchor members are locked together). It will be understood that use of a small number of sutures (e.g., one or two) will require engagement of the proximal-most groove 30a while use of a greater number of sutures will require engagement of the distal-most groove 30b. In the preferred embodiment two grooves 30, longitudinally spaced along axis 210, have been found sufficient to exert an acceptable amount of compressive force over the range of one to three stands of #2 suture for which anchor 10 was designed. The compressive force is applied between compressive surface 19 at the distal end of eyelet 28 and annular compressive surface 59 at the distal end of outer anchor member 14.

Figure 5:
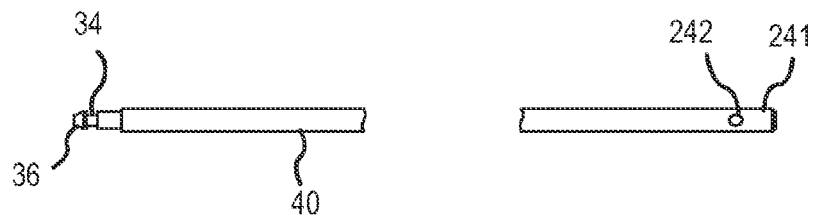
FIG. 5 is a side view of the actuator shaft.
Figure 6:
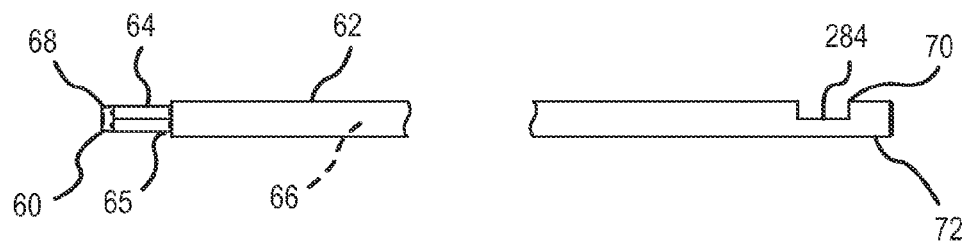
FIG. 6 is a side view of the driver shaft.

As shown in FIGS. 5 and 6, inner and outer connecting shafts 40 and 62 serve to support inner and outer anchor members at the distal end of driver 200 while enabling the anchor members to be manipulated by the handle at the proximal end of driver 200. Outer anchor member 14 is slidably mounted on the distal end 60 of drive shaft 62 (best seen in FIG. 6). Distal end 60 is provided with a coaxial extension 64 having a hexagonal cross-section which mates with proximal portion 56 of the lumen of outer anchor member 14. Drive shaft 62 has an axial lumen 66 which is large enough to slidably receive actuator shaft 40 (best seen in FIG. 5). Thus, both inner and outer members 12 and 14 are situated in coaxial alignment with each other at the distal ends of their respective coaxial shafts. The proximal ends of each of the shafts are attached to handle 204 of driver 200. Drive shaft 62 also has a conical tip 68 at its distal end and a keying feature 70 at its proximal end 72, the functions of which will be understood below. The conical tip 68 is used as a retention mechanism which operates by creating a friction fit with the distal cylindrical lumen 54 of outer anchor member 14. When outer member 14 is placed on the distal end of drive shaft 62 the hexagonal lumen portion 56 will be received on distal end 64 with the proximal end of outer member 14 in abutment with shoulder 65. The dimensions of the anchor and driver components are such that, when this happens, conical tip 68 will extend slightly into cylindrical lumen 54 in order to create a friction fit. This secures outer member 14 to prevent its unintended dislodgement from the drive shaft during manipulation, such as during the step of inserting the anchor into the bone tunnel.

As mentioned above, inner and outer anchor members 12 and 14 are components of anchor 10 which is designed to be anchored in a bone at a surgical work site, and also designed to be deployed in order to engage a suture without the need to tie a knot. The method of using the invention to place and deploy anchor 10 at the work site, and the elements necessary to carry out the method are best understood by reference to the features and functions of driver 200 which essentially comprises handle 204, drive shaft 62 and actuator shaft 40. Driver 200 includes means for positioning suture anchor 10, advancing the threaded sleeve 50 of the anchor into bone and deploying and locking suture anchor 10, thereby securing the suture between the distal end 59 of the threaded sleeve 50 of outer member 14 and the compressive surface 19 at the distal side of eyelet 28 of inner member 12 as well as between the anchor and the wall of the bone tunnel (best seen in FIG. 20).

Driver Handle Structure

Figure 13:
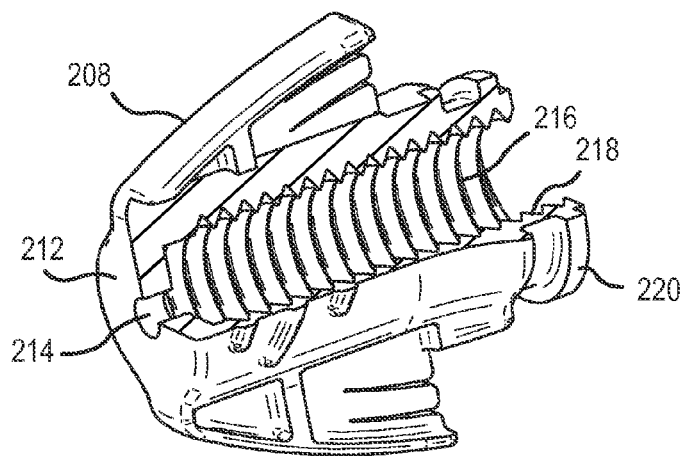
FIG. 13 is a perspective view of the carrier housing of the driver handle member, partially in cross-section.

As best seen in FIGS. 1, 10 and 13, handle 204 comprises a main body 206 and carrier housing 208 which is rotatable relative to main body 206 about axis 210. Carrier housing 208 has a body 212 with a distal, coaxial aperture 214 which is sized to slidably receive drive shaft 62. Body 212 also has a coaxial bore 216 having threads 218. A proximal flange 220 is adapted to be received proximally of flange parts 222a and 222b in order to allow relative rotation between carrier housing 208 and main body 206 while preventing translation between them. Main body 206 comprises a left handle housing 227 and a right handle housing 228. The left and right housings are not exact mirror images of each other because each has unique internal molded features designed to implement certain functions of the invention. It will be understood, however, that the description of one of the housings will for the most part be sufficient to describe the other.

With respect to the function of driving inner anchor member 12 via actuator shaft 40, handle 204 receives the proximal end 241 of shaft 40 via the axial lumen 66 of drive shaft 62. Proximal end 241 has a transverse bore 242 which receives a pin 243 to couple shaft 40 to actuator coupling 244. Coupling 244, best seen in FIG. 14, comprises a shaft 260 having a transverse indicator disc 262 at its proximal end and an axial bore 264 at its distal end 266 to receive the proximal end of shaft 40. Shaft 260 has a reduced diameter portion 267 bounded by transverse distal and proximal force-receiving surfaces 268, 269, respectively. As will be explained below, these surfaces are instrumental in deploying anchor 10.

Figure 11:
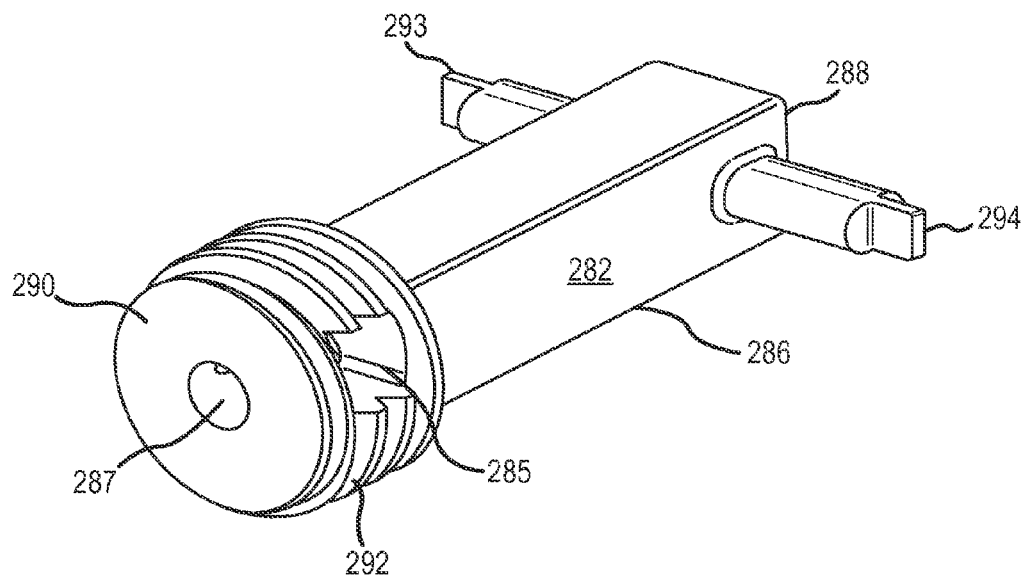
FIG. 11 is a perspective view of the transport spindle of the driver handle.
Figure 12:
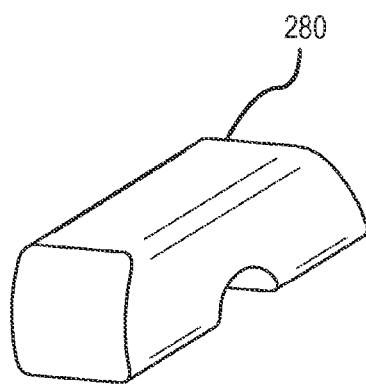
FIG. 12 is a perspective view of the key retainer of the driver handle.

With respect to the function of driving outer anchor member 14 via drive shaft 62, handle 204 receives the proximal end 72 of shaft 62 and couples it in a non-rotating manner via key 280 to spindle 282. Shaft 62 has a notch 284 near its proximal end 72. Notch 284 is designed to be aligned with transverse aperture 285 when the proximal end 72 of shaft 62 is properly assembled with spindle 282. In this position, key 280 will matingly fit with notch 284 to lock shaft 62 to the spindle, both rotationally and translationally. Spindle 282, best seen in FIG. 11, has a rectilinear body 286, proximal end 288 and a distal end 290, the latter being provided with a threaded portion 292. Proximal end 288 is provided with two diametrically opposed proximity indicators 293 and 294, the function of which will be understood below. Spindle 282 also has an axial lumen 287 passing entirely through spindle 282 to allow passage of actuator shaft 40 along axis 210. Spindle body 286 is received in recess 288 formed in right housing 228, the recess being sized to receive the rectilinear body 286 so as to make spindle 282 rotatable with handle 204. A mirror image of the recess (not shown) is formed in left housing 227. Each recess has an elongated longitudinally extending indicator window 290 adapted to receive or allow visibility of the outer end of one of the associated proximity indicators 293, 294 so it is visible from the outside of either side of handle 204. Threaded portion 292 is adapted to engage threaded bore 216 of carrier housing 208 (best seen in FIG. 13) in order to enable rotation and translation of outer anchor member 14 as handle main body 206 is turned about axis 210. The pitch of thread 292 matches the pitch of thread 218 which matches the pitch of the outer anchor body thread 50. By having main body 206 fixedly coupled to shaft 62, rotating main body 206 will cause rotational motion of shaft 62 and preventing rotation of carrier housing 208 will cause translation of main body 206. This in turn will cause rotational and translational motion of outer anchor member 14, thus causing it to rotate relative to the bone tunnel and slide along hexagonal lumen section 56 to rotationally and translationally advance threaded sleeve 50 longitudinally. (Preventing rotation of carrier housing 208 enables it to serve as a reference point for the advancement of the anchor.)

Figure 8:
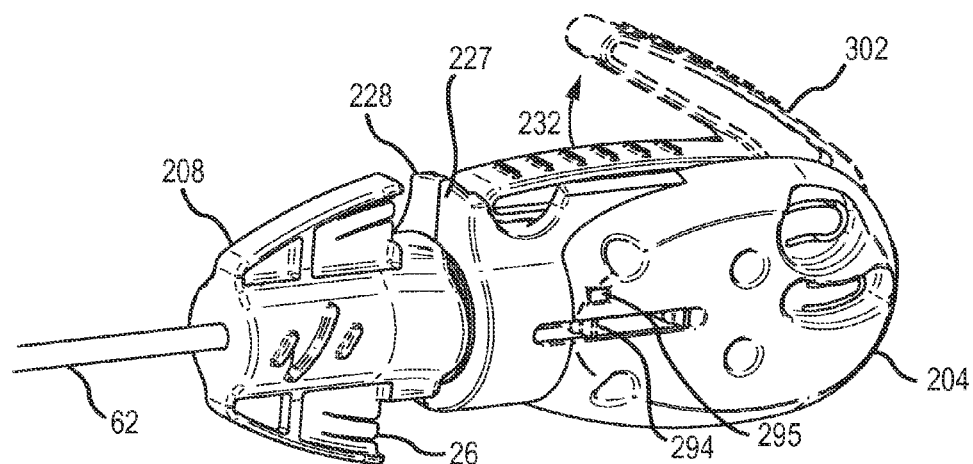
FIG. 8 is a perspective view of the handle of FIG. 1 with the trigger lever in the second position.
Figure 18:
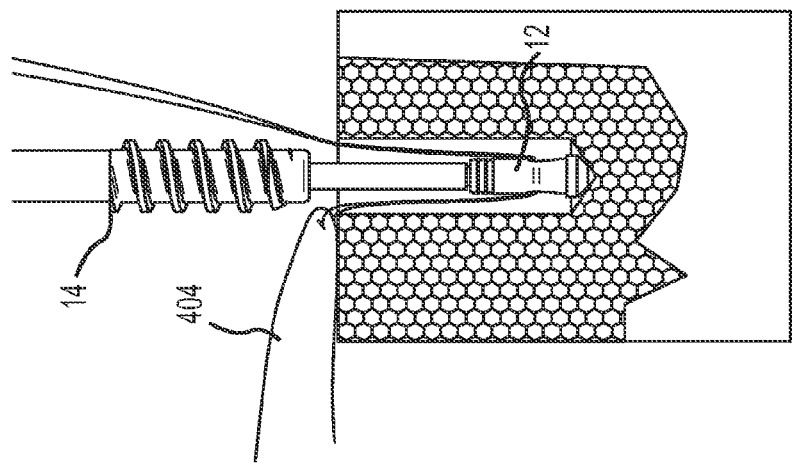
FIG. 18 is a diagrammatic view of the anchor tip, suture and tissue to be repaired with the anchor tip bottomed out in the bone hole and the tissue approximated to bone during a portion of the method of using the invention.
Figure 26C:
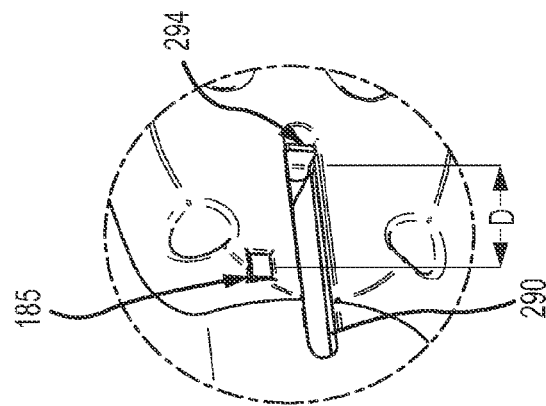
FIG. 26C shows the position of the proximity indicator when the anchor components are in the position of FIG. 26A.
Figure 26B:
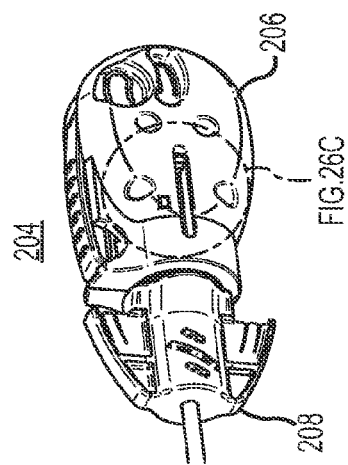
FIG. 26B shows the position of the handle component of the invention when the anchor components are in the position of FIG. 26A.
Figure 26A:
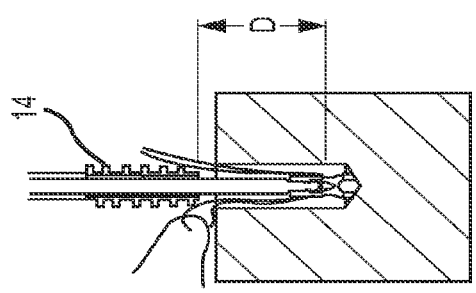
FIG. 26A shows the position of anchor components of the invention relative to a bone tunnel immediately prior to placement of the outer anchor member component into the bone tunnel.

As will be understood below, the purpose of proximity indicators 293, 294 is to provide, from outside the surgical work site, a visual indication of the location of the distal end 59 of outer anchor member 14 relative to the proximal end of eyelet 28 of inner anchor member 12. The proximity indicators 293, 294 slide distally within their associated proximity window 290 from a starting, proximal-most position (as shown in FIG. 1), to an ending, distal-most position as shown in FIG. 8. Certain elements such as trigger lever 302 and proximity indicator 294 are shown in FIG. 8 in solid lines and in phantom lines to indicate their positions relative to handle 204 at different points in the process of using the invention. That is, proximity indicators 293, 294 indicate that when the outer member is placed relative to the bone tunnel as shown in FIGS. 18 and 26A (i.e., when the distal end of the outer anchor member 14 is slightly spaced above the bone tunnel) moving the indicators a certain distance to align them to the target zone indicator 295 will align the proximal end of outer member flush with the surface of the bone in the position shown in FIG. 19, and distal end 59 will be aligned with compressive surface 19 which location is represented by the proximity indicators 293, 294 being aligned with the proximal side of target zone indicator 295, best seen in FIG. 27B.

It will be understood that other indicating elements may be used other than proximity indicators 293, 294 and target indicator 295. These indicating elements 293, 294 and 295 serve to communicate to the user the extent of movement of outer member 14 relative to inner member 12 by use of a component visible on the surface of handle 204. This movement can be expressed in a specific distance of travel (16 to 18 mm) of the outer member 14. Other mechanisms could be devised to communicate this information to the user. Such mechanisms could indicate when a component, other than spindle 282, fixedly connected to outer member 14 has moved a predetermined distance. Another possible indicator mechanism could be indicia of some kind on either the inner or outer anchor members 12 or 14 where such indicia could be visible through an endoscope used to view the worksite. Such indicia (e.g., lines, dots, scale, etc.) could identify how much the inner and outer members have moved relative to each other.

Trigger Mechanism

Figure 9:
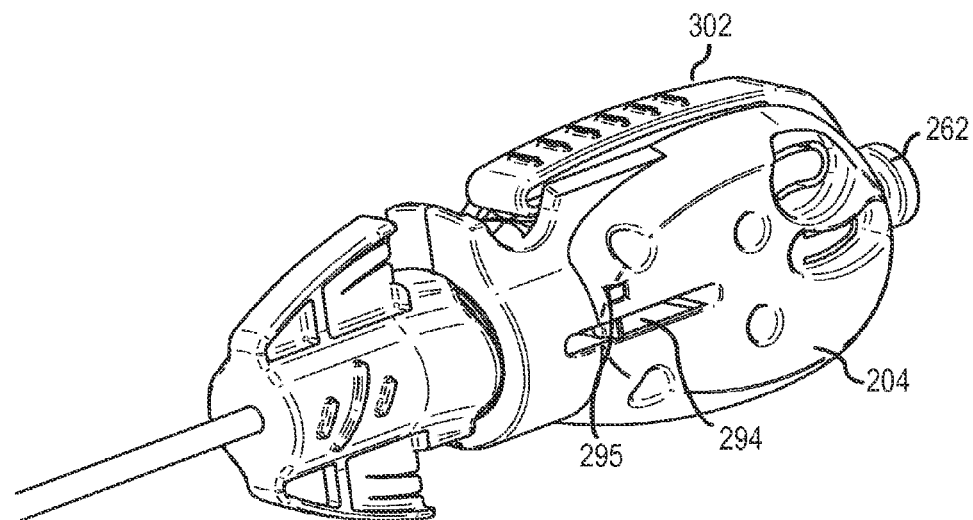
FIG. 9 is a perspective view of the handle of FIG. 1 with the trigger lever in the third position.
Figure 20:
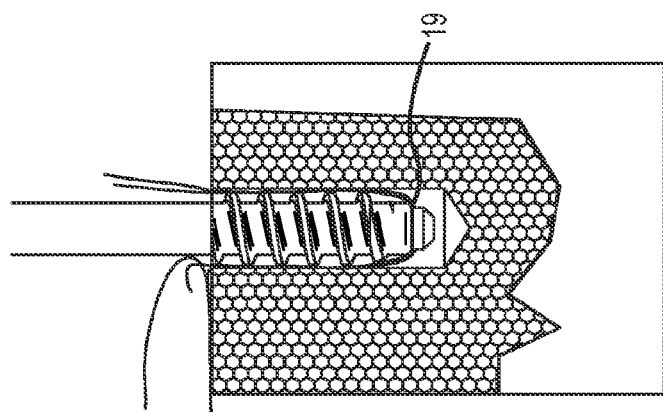
FIG. 20 is a diagrammatic view of the final configuration of the deployed (i.e., suture locked) anchor position during a portion of the method of using the invention.
Figure 19:
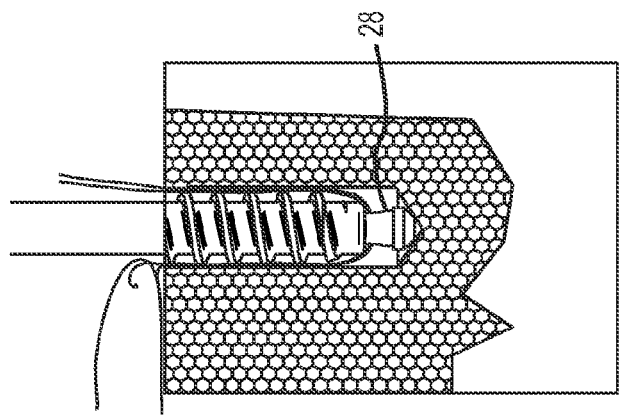
FIG. 19 is a diagrammatic view of the anchor with the outer threaded body advanced over the inner member and flush with the bone surface during a portion of the method of using the invention.
Figure 21:
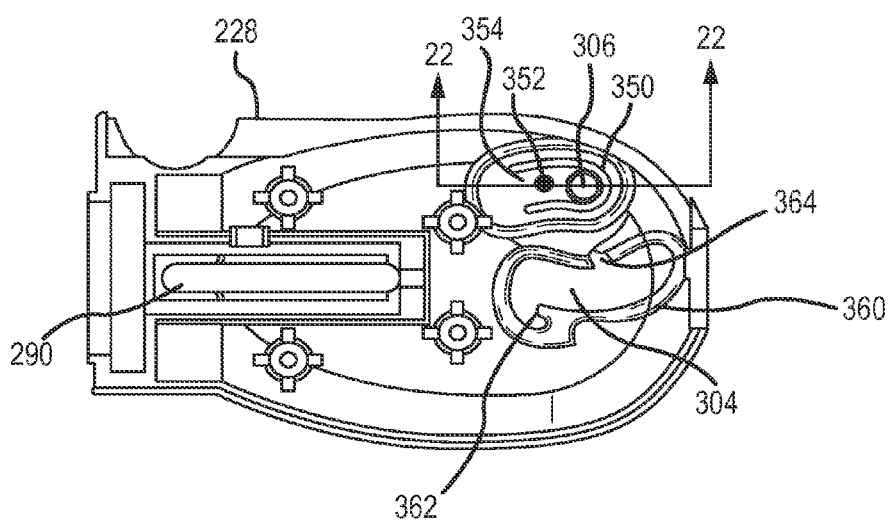
FIG. 21 is a side elevation view of internal parts of the right handle housing with some components omitted for clarity.
Figure 22:
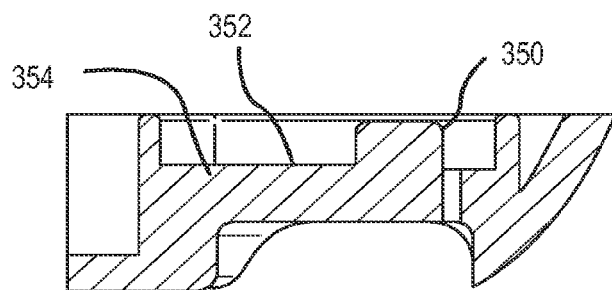
FIG. 22 is a cross-section view of the handle showing the flexible arm with post taken along the line 22-22.
Figure 23:
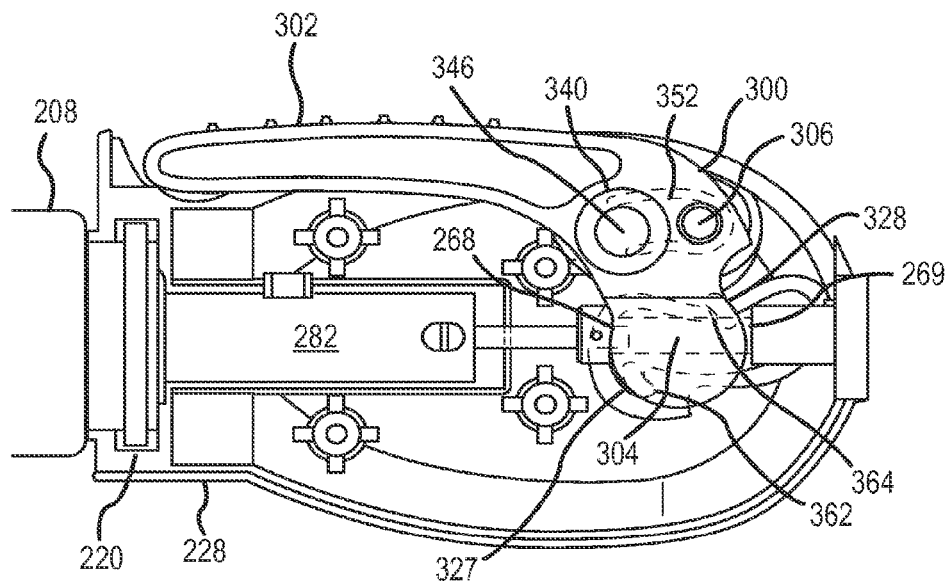
FIG. 23 is a side elevation view of the right handle assembly of FIG. 21 with some components in place and showing the trigger lever in the first position.
Figure 24:
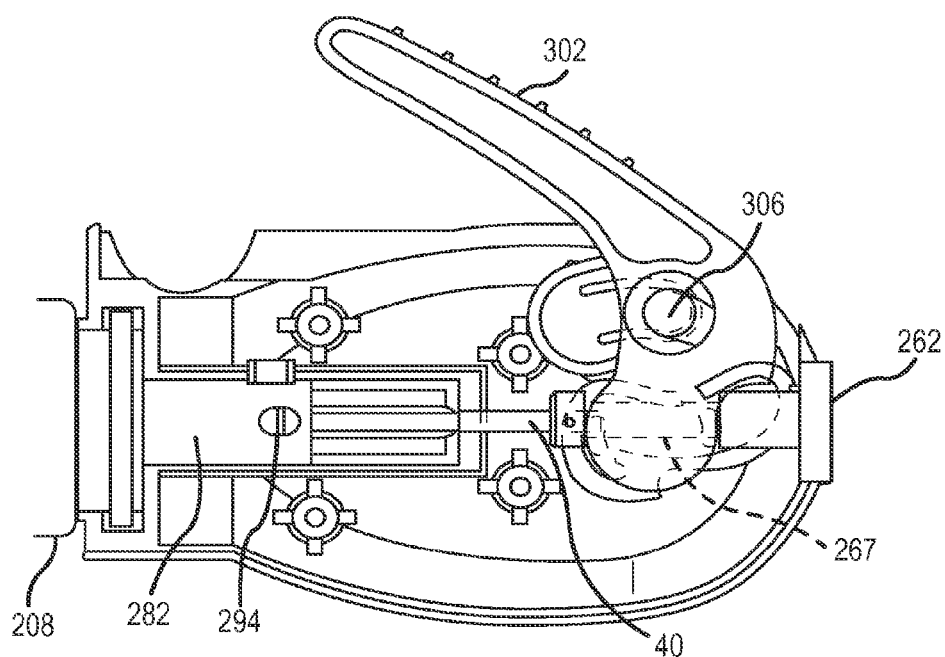
FIG. 24 is a view of FIG. 23 with the trigger lever shown in the second position.

Once outer anchor member 14 has been advanced far enough into the bone tunnel, i.e., to the position shown in FIG. 19, and a determination has been made that anchor 10 is properly positioned and tensioned, anchor 10 may be deployed to the position shown in FIG. 20. With respect to the function of deploying anchor 10 by engaging and compressing together inner and outer anchor members 12 and 14, handle 204 is provided with a trigger mechanism 300 designed to be selectively engaged with inner anchor member 12, to prevent premature activation of the inner anchor member and to deploy it only at the proper time. Trigger mechanism 300 comprises a trigger lever 302 having a unique dual pivot axis structure best understood by references to FIGS. 21-25. The trigger mechanism is operable through three positions as represented in FIGS. 1, 8 and 9. In the starting, first trigger position, trigger lever 302 lies against the body of handle 204 as shown in FIGS. 1 and 23. Cocking the trigger by pulling the trigger lever 302 in direction 232 up to a second trigger position as shown in FIGS. 8 and 24 causes trigger lever 302 to pivot about first pivot axis 304 and produces tactile and audible feedback due to pins 50 engaging ramp surfaces 348 and snapping into hollow spaces 346, 347 (as described below). Trigger lever 302 will then automatically engage a second pivot axis 306. Squeezing trigger lever 302 to move it counterclockwise about this second pivot axis 306 will actually move inner anchor member 12 proximally and place lever 302 and handle 204 into the third trigger position shown in FIGS. 9 and 25. This also causes the user to receive tactile and audible feedback and visual confirmation of anchor deployment and suture locking. The visual confirmation is denoted by the disc 262 which protrudes from the proximal end of the handle upon successful anchor deployment. Simultaneously, the frangible connection on actuator shaft 40 at location 32 is broken whereby driver 200 is detached from inner anchor member 12 allowing the user to remove the driver, leaving the deployed anchor and sutures in place.

Dual Pivot

Figure 15:
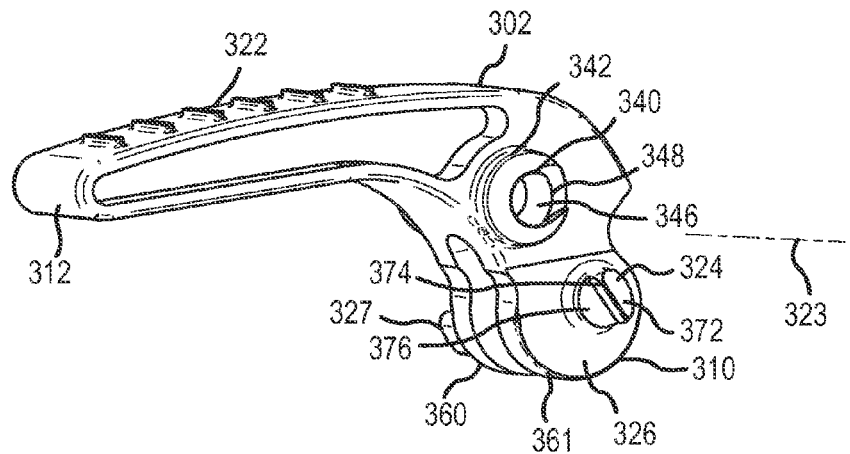
FIG. 15 is a left perspective view of the trigger lever.
Figure 16:
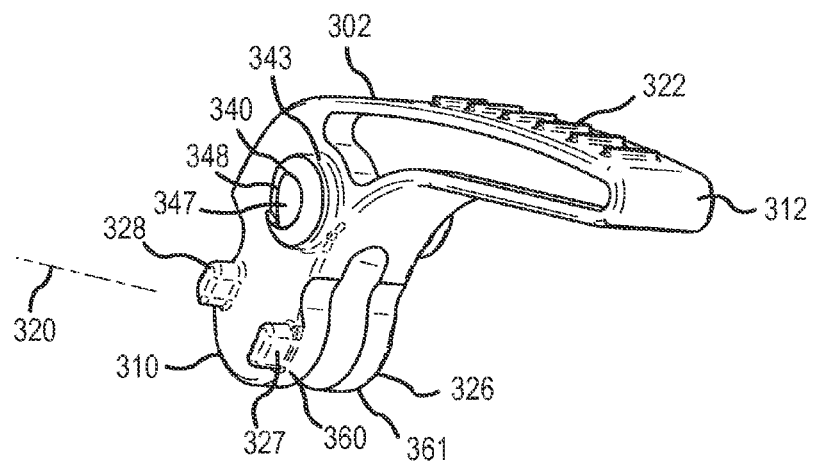
FIG. 16 is a right perspective view of the trigger lever.

The aforementioned trigger lever positions are achievable due to the unique dual pivot axis design of trigger mechanism 300. The trigger mechanism has two distinct pivot locations with structures which allow trigger lever 302 to pivot, first, about a first trigger axis and, second, about a second pivot axis. The pivoting action of trigger lever 302 is enabled only when the first and second trigger axes are coincident with first and second pivot axes, respectively, defined by specific locations on the main body 206. Trigger lever 302, best seen in FIGS. 15 and 16 is elongated and has a proximal end 310, a distal end 312 and a first trigger axis 320 situated between the proximal and distal ends. The trigger lever 302 has a lever portion 322 at distal end 312 and a base portion 326 at proximal end 310. The base portion 326 has elements (explained below) which establish the first trigger axis 320. The right side of trigger lever 302 has two spaced, laterally extending projections 327, 328 which are symmetrical about and define axis 320. At another point between the proximal and distal ends of trigger lever 302, trigger lever 302 is provided with a pair of opposed, laterally outwardly extending hollow pins 340 and 341 coaxially aligned with second trigger axis 323. Each pin 340 and 341 is formed of a cylindrical body 342, 343, respectively, having a cylindrical wall, a rim and a hollow interior space 346, 347 wherein each interior space serves as a pivot recess. The proximal side of the rim of each cylindrical wall is provided with a ramp surface 348 inclined laterally outwardly from its proximal side to its distal side adjacent the hollow interior spaces 346, 347.

As mentioned above, the pivoting action of trigger mechanism 300 requires the first and second trigger axes to be coincident with first and second pivot axes. The first and second pivot axes 304 and 306 are defined relative to elements on left and right housings 227 and 228. The first and second trigger axes are defined relative to elements on trigger lever 302. The first pivoting action of trigger lever 302 is operable when the first pivot axis 304 is coincident with the first trigger axis 320 and the second pivoting action is operable when the second pivot axis 306 is coincident with the second trigger axis 323.

The transition of trigger lever 302 from being pivotable about one axis to then being pivotable about another axis is demonstrated by FIGS. 21-25. The right and left handle housings 228 and 227 each have a laterally inwardly extending pivot pin 350 which is molded into or attached to the end of its associated flexible arm 352. Each arm 352 is hinged at its distal end 354 and is preferably arcuately shaped. The radius of curvature of each arm 352 is preferably equal to the distance between the curved center line (not shown) of arm 352 and first pivot axis 304. First pivot axis 304 is the midpoint between projections 327 and 328. Right handle housing 228 is provided with a curvilinear wall 360 provided with retaining gaps 362 and 364 designed to receive the aforementioned projections 327 and 328, respectively. These gaps help to avoid premature translation of actuator shaft 40 by preventing coupling 244 from moving so long as the trigger lever is down. The wall 360 constrains projections 327, 328 until pivoting of the lever about axis 304 is complete, and then the wall enables proximal motion of the projections (and base portion 326) when lever 302 is pivoted counterclockwise about axis 306. Trigger lever 302 is mounted between left and right housings 227, 228 and as trigger lever 302 is pivoted clockwise (when viewed as in FIG. 21) about first pivot axis 304, the rims of pivot pins 340 and 341 slide along their associated arms 352. (It should be noted that the pins need not contact the arms and their unbiased position they may be slightly above the arms.) As each pin nears the proximal end of its respective arm 352, the pins will encounter ramp 348 causing its associated arm 352 to flex laterally outwardly momentarily to clear pins 340, 341. Further clockwise motion of trigger lever 302 will cause pins 350 to snap back (laterally inwardly) into the recesses 346, 347, respectively, within each pivot pin whereby a new, second pivot axis 306 will be established for trigger lever 302 as best seen in FIG. 24. The diameters of pins 350 and recesses 346, 347 are substantially similar in order to enable creation of pivot axis 306.

Figure 25:
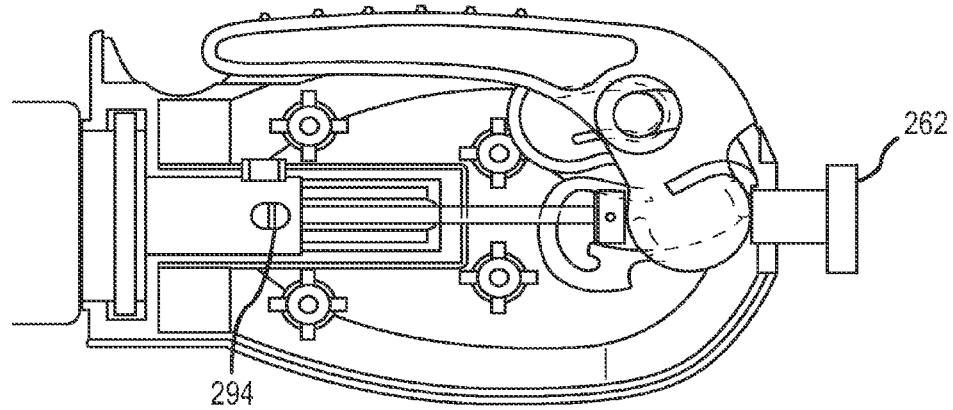
FIG. 25 is a view of FIG. 23 with the trigger lever in the third and final position.

The base 326 of trigger lever 302 is provided with a pair of parallel, semi-circular projections 360 and 361 adapted to pivot around second pivot axis 306 along with sound pin 324. As will be understood below, projections 360 and 361 straddle shaft 267 so as to sequentially engage the transverse actuating surfaces 268 and 269 on coupling 244. The outer perimeter of each of the projections 360, 361 serves as a semi-circular bearing-like surface which actually engages the associated actuating surfaces 268, 269 thereby pushing inner anchor member 14 proximally as best seen in FIG. 25. Sound pin 324 (omitted for clarity in FIGS. 23-25) is situated on the left side of trigger lever 302 so as to pivot around second pivot axis 306 and slide (again, there could be a slight gap) proximally along its associated flexible arm 370. Arm 370 has a laterally inwardly extending pin (not shown) at its proximal end. The pin on arm 370 is engaged by a ramp surface 372 on the proximal side of sound pin 324. As trigger lever 302 nears the end of its counterclockwise motion about pivot axis 306 the pin on arm 370 will ride up ramp 372 (similarly to pins 350 riding up ramp 348 on their respective flexible arms 352) until it clears the top 374 of the ramp and snaps laterally inwardly onto flat surface 376. It will be understood that this arrangement provides a tactile and audible indication of the completion of the deployment of anchor 10 while disc 262 at the proximal end of coupling 244 provides a visual indication.

Figure 17:
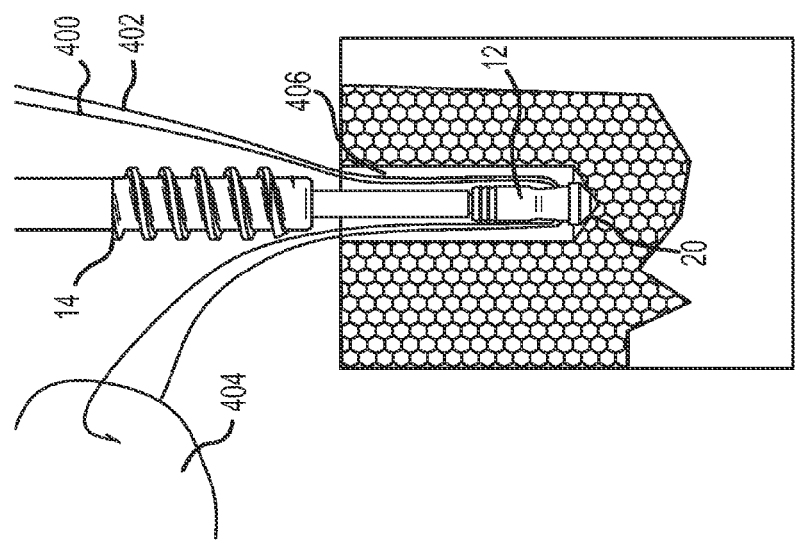
FIG. 17 is a diagrammatic view of the anchor tip, suture and tissue to be repaired with the anchor tip bottomed out in the bone hole during a portion of the method of using the invention.

FIGS. 23-25 show the sequence of operation of trigger mechanism 300 about the first and second pivot axes 304 and 306 defined by pivot projections 327, 328 and pins 340, 341 respectively. Initially, trigger lever 302 is situated in a rest position with lever 302 lying adjacent the body of handle 204 as shown in FIG. 23. In this position, trigger lever 302 is poised to pivot about axis 304. The actual pivoting of trigger lever 302 occurs by the user lifting lever 302 away from handle 204. This action would also cause flexible arm 352 to flex laterally outwardly from each housing 227, 228 until it could snap back into opposing recesses 346, 347 in projections 341, 342, resulting in the "ready" or cocked position shown in FIG. 24. In this position the trigger lever 302 has a new pivot axis 306 such that pressing lever 302 toward handle 204 will cause projections 360, 361 of base 326 to straddle section 267 of coupling 244 and pivot about axis 306. This causes projections 360, 361 to engage the proximal most transverse actuating surface 269 attached to the proximal end of the coupler 244 at the end of actuator shaft 40, thus moving indicator disc 262 proximally to provide a visual indication of anchor deployment. The operation of driver 200 is explained by reference to the various possible positions of trigger lever 302 relative to other components in the system. Thus, the first trigger lever position will be defined as the position of the components at the point in time when trigger lever 302 lies along the handle as shown in FIG. 23, which corresponds to the proximity indicators 293, 294 being at the proximal-most position as shown in FIG. 1, which corresponds to the outer anchor member 14 prior to its engagement with the suture as shown in FIG. 17. In this first position the two projections 327, 328 situated on one side of trigger lever 302 engage walled section 360 in the right housing 228. Receiving recesses 362 and 364 engage projections 327, 328 and help to hold the trigger and inner anchor member in place as best seen in FIG. 23. The second trigger lever position is defined as that corresponding to FIGS. 8, 19 and 24 which prepare handle 204 to be placed in a condition ready to retract the inner anchor member 12 into engagement with the outer anchor member 14. This latter condition corresponds to position three seen in FIG. 25.

Method of Driver Operation

The method of using the invention to determine the relative positions of the components of the anchor and the driver is best understood by reference to FIGS. 1, 17-20 and 25-29. To start, the user first creates a bone tunnel 406 of known depth, generally 17-19 mm, and passes one end of suture 400 through tissue 404 to be anchored to the site. Both free suture limbs 400 and 402 are then passed through loading loop 300 which is used to draw the suture limbs through eyelet 28 at the distal tip of the suture anchor. Loop 300 is attached to a handle 302 which is removably clipped on to actuator shaft 40 via clip 304. After the suture is threaded through eyelet 28, the loop and clip are removed. The anchor components are then advanced into the preformed bone hole 406 with the driver until the anchor's distal tip 20 contacts the floor of the hole (as best seen in FIG. 17). The proximity indicator 294 is in the position shown in FIG. 1. While holding the anchor stationary the suture is tensioned until the tissue 404 is approximated to the bone and the desired tissue position is achieved (as best seen in FIG. 18). To maintain this position, the free suture limbs are secured using the cleats 213 in the carrier housing 208. At this point the tension in the suture causes suture limbs 400, 402 to lie transversely across the proximal end of eyelet 28. Since the position of the suture at the proximal end of eyelet 28 is the position ultimately desired in order to optimize the friction fit holding the suture in place, the following steps of this method are intended to secure the suture in this position and transfer the tension in the suture from the cleats to the suture anchor. This is done by engaging the outer anchor member with the bone tunnel thereby compressing the suture against the bone tunnel wall. The outer anchor member is advanced into the bone tunnel until it is flush with the surface, thereby maximizing the amount of suture compressed between the wall and the anchor. To achieve this, the outer anchor member must be advanced a distance D which is, as shown in FIG. 26A, the distance between the position of the distal end 59 of outer anchor member 14 and the suture at the proximal end of eyelet 28. This is equal to the distance between the initial starting position of proximity indicator 293, 294 and target zone indicator 295.

Figure 27C:
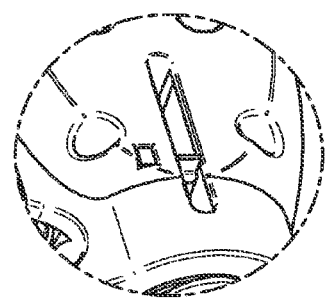
FIG. 27C shows the position of the proximity indicator when the anchor components are in the position of FIG. 27A.
Figure 27B:
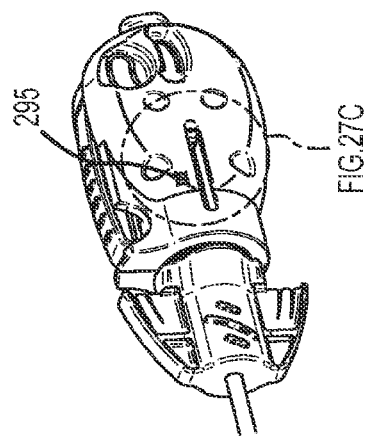
FIG. 27B shows the position of the handle component of the invention when the anchor components are in the position of FIG. 27A.
Figure 27A:
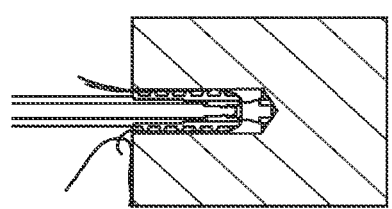
FIG. 27A shows the position of anchor components of the invention relative to a bone tunnel after advancement of the outer anchor member component of the suture anchor.
Figure 28C:
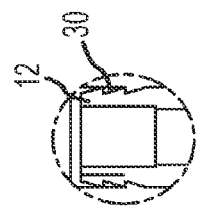
FIG. 28C shows an exploded view of a portion of FIG. 28B showing the locking engagement between inner and outer anchor members by use of the distal-most groove on the inner member.
Figure 28D:
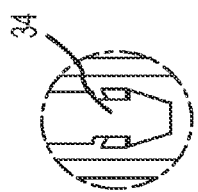
FIG. 28D shows an exploded view of a portion of FIG. 28B showing the engagement of the inner anchor member with the frangible connection to its actuator shaft.
Figure 28E:
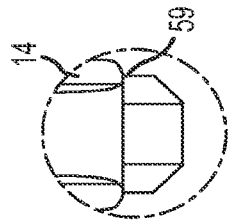
FIG. 28E shows an exploded view of a portion of FIG. 28B showing the compression of suture between the proximal end of the outer anchor member and the compressive surface at the distal end of the eyelet of the inner anchor member.
Figure 28B:
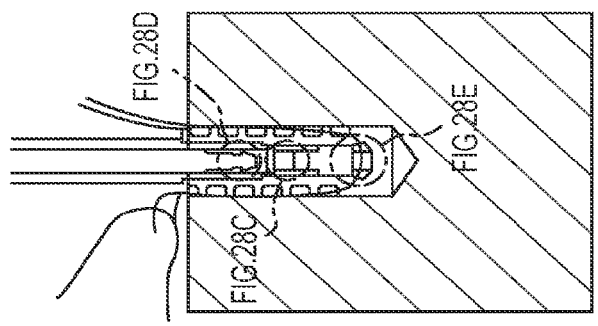
FIG. 28B shows the position of the anchor components when the handle has been activated as shown in FIG. 28A.
Figure 28A:
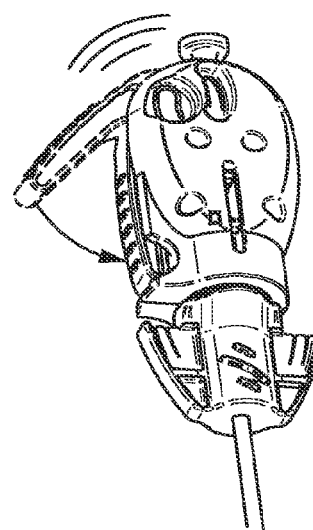
FIG. 28A shows the position of the handle component of the invention after completion of the deployment of the inner anchor member.

Proximity indicators 293, 294 facilitate determination of the anchor's position in the bone tunnel. Initially the proximity indicators 293, 294 will be situated at the proximal end of their respective proximity indicator window 290 as shown in FIGS. 1 and 26C. Next, the threaded outer body 14 of anchor 10 must be advanced over the inner anchor member 12 to deploy anchor 10. This is done by holding the carrier housing 208 stationary while rotating the handle 204 clockwise until the outer anchor member 14 is flush with the bone surface (best seen in FIGS. 19 and 27A). This position will be indicated when the proximity indicators are aligned with the target zone indicator 295, as shown in FIG. 27B, at which point the user will know that the outer member 14 is at the position shown in FIG. 27A, flush with the bone surface and aligned with the suture situated at the proximal end of eyelet 28. At this point trigger mechanism 300 can be cocked so that actuator shaft 40 can be retracted proximally to thereby deploy the inner anchor member 12 by moving it proximally to crimp the suture between the compressive surface 19 of the inner anchor member 12 and the distal end 59 of outer anchor member 14 (best seen in FIG. 20). At this point the inner and outer members are locked together in a suture-locked configuration by the engagement of either groove 30a or 30b with projections 58.

Figure 29A:
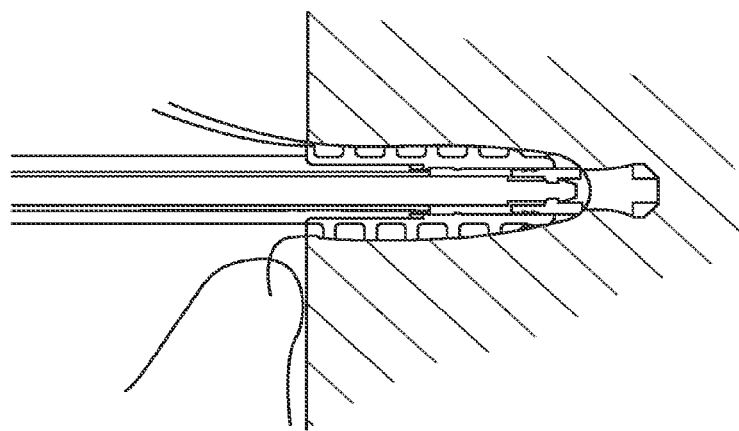
FIGS. 29A and B show a potential position of certain components if the suture anchor is not properly inserted.
Figure 29B:
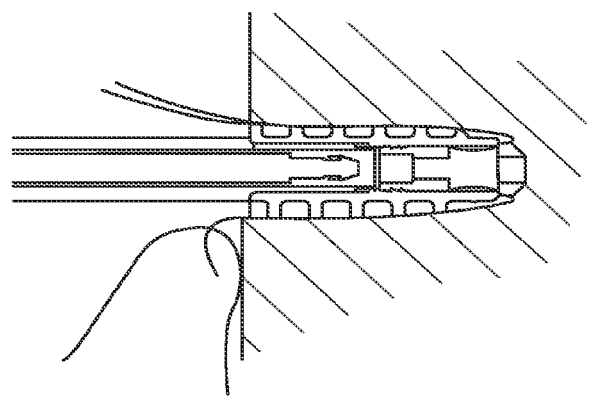

FIGS. 29A and B and 30A and B show the consequences of operating outside the range of motion of the proximity indicator and deploying inner anchor member either too deep in a bone hole or too shallow, respectively. In FIG. 29A the inner anchor member is inserted to the bottom of a bone hole that is too deep, and the outer anchor member is then advanced so as to be flush with the surface of the bone. This causes the suture, when properly tensioned, to lie across the proximal end of eyelet 28. However, because the eyelet is too far away from the distal end 59 of the outer member, when the inner member is deployed by moving it proximally to compress the suture and lock the inner and outer members together there will be too much laxity in the suture as shown in FIG. 29B. This results in decreasing the total frictional holding force provided by the anchor. That is, the frictional engagement is only present in the areas where the suture is captured between outer member 14 and the bone tunnel wall, and not at the distal end of the anchor.

Figure 30A:
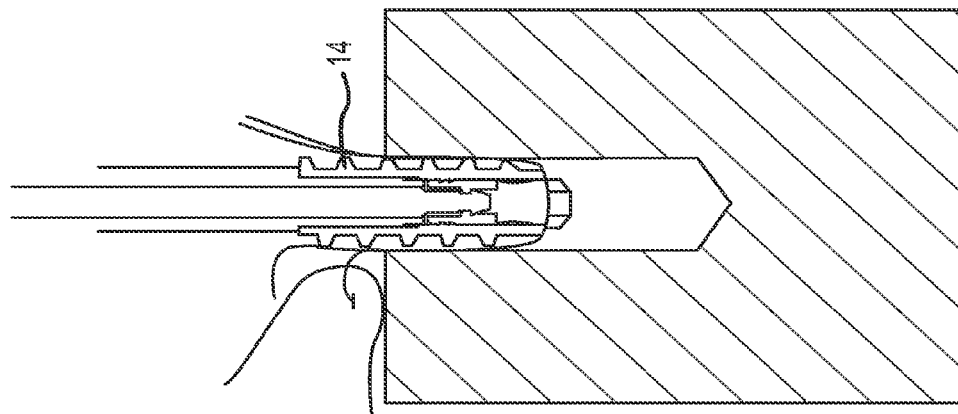
FIGS. 30A and B show an alternative arrangement of a potential position of certain components if the suture anchor is not properly inserted.
Figure 30B:
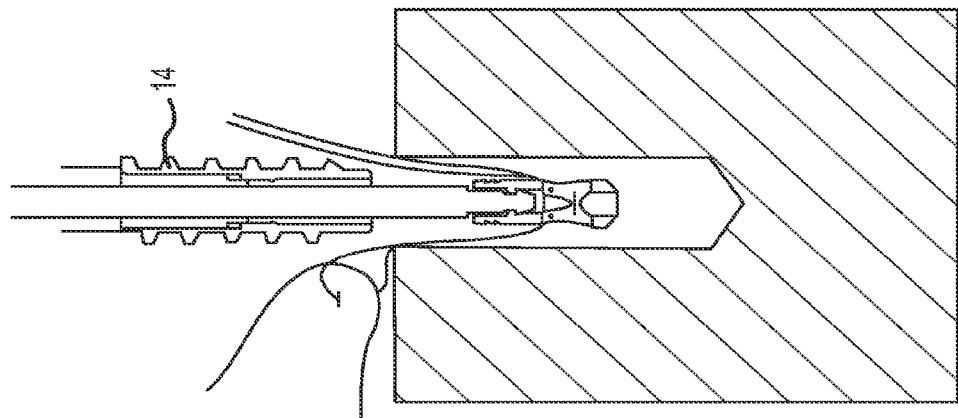

In FIG. 30A the eyelet and distal tip of anchor 10 are not inserted deep enough into the bone. Under this circumstance there is not enough suture available to reach the bottom of the hole after the soft tissue has been approximated. Subsequent advancement of outer anchor member 14 cannot be made flush with the bone surface, thereby decreasing the surfaces over which friction is provided, thereby decreasing the frictional forces holding the suture against the bone tunnel wall. Also, the anchor stands proud, which is undesirable, and further advancement of the anchor body is impeded by frictional forces of the suture against the bone.

While outer anchor member 14 is shown with a threaded outer surface requiring rotation of the outer member 14 about axis 210 in order to advance the outer anchor member toward the inner anchor member to thereby lock the component parts together, it is contemplated that a non-rotatable design could also be used to simply advance the outer member toward the inner member without rotation to thereby lock the components together. The thread on the outer surface of a rotatable device is sometimes referred to as a projection for being embedded in the bone wall, and annular ribs or outwardly extending barbs, etc. are also deemed projections.

It will be understood that grooves 30 could be actual grooves or could, in cross-section, be in the form of a ratchet and pawl structure (best seen in FIG. 28C) facilitating flexure of projections 59 when moving proximally and then preventing backwards movement in a distal direction.

It will be understood by those skilled in the art that numerous improvements and modifications may be made to the preferred embodiment of the invention disclosed herein without departing from the spirit and scope thereof.

What is claimed is:

1. A knotless suture anchor assembly for engaging a bone tunnel and holding suture therein to knotlessly secure said suture to soft tissue comprising:
   an elongated generally cylindrical hollow outer member having an axial lumen, an outer surface with projections for engaging the wall of the bone tunnel, a distal end and a proximal end;
   an elongated, generally cylindrical inner member having an axis, a proximal end and a distal end, said distal end having a transverse passage for receiving suture therethrough, said transverse passage having a proximal and distal end and adapted to receive a plurality of sutures in said eyelet, said inner member adapted to move coaxially relative to said outer member between a distal, suture-unlocked position and a proximal, suture-locked position;
   a suture joining said soft tissue to said anchor, said suture directed along a path from soft tissue to said bone tunnel, between said outer member and the wall of said bone tunnel, through said transverse passage, and proximally between said outer member and the wall of said said bone tunnel;
   a locking means interposed between said inner and outer members, said locking means coaxially movable between a suture-unlocked configuration, in which said inner member is moveable relative to said outer member so said suture is slidable along said path, and a suture-locked configuration in which movement of said inner member relative to said outer member is prevented and said suture is crimped between said distal end of said eyelet and said distal end of said outer member;

means for moving said inner member proximally from said suture-unlocked position toward said suture-locked position wherein said suture is crimped between said inner and outer members; and means for moving said outer member distally from said suture-unlocked position toward said suture-locked position;

means for locking said inner member to said outer member to maintain said inner and outer members in said suture-locked position.

2. The knotless suture anchor assembly according to claim 1 wherein said locking means is able to be selectively activated to lock a selected number of sutures ranging from one to three.

\* \* \* \* \*